(12) United States Patent
Isaza

(10) Patent No.: US 11,904,093 B2
(45) Date of Patent: Feb. 20, 2024

(54) VENTILATOR GAS DELIVERY INITIATION VIA A VIRTUAL PRESSURE TRIGGERING MECHANISM

(71) Applicant: KONINKLIJKE PHILIPS N.V., Eindhoven (NL)

(72) Inventor: Fernando Jose Isaza, Carlsbad, CA (US)

(73) Assignee: Koninklijke Philips N.V., Eindhoven (NL)

( * ) Notice: Subject to any disclaimer, the term of this patent is extended or adjusted under 35 U.S.C. 154(b) by 1067 days.

(21) Appl. No.: 16/632,192

(22) PCT Filed: Jul. 12, 2018

(86) PCT No.: PCT/EP2018/068872
§ 371 (c)(1),
(2) Date: Jan. 17, 2020

(87) PCT Pub. No.: WO2019/016055
PCT Pub. Date: Jan. 24, 2019

(65) Prior Publication Data
US 2020/0171254 A1 Jun. 4, 2020

Related U.S. Application Data

(60) Provisional application No. 62/533,691, filed on Jul. 18, 2017.

(51) Int. Cl.
| | | |
|---|---|---|
| A61M 16/00 | (2006.01) | |
| G05B 17/02 | (2006.01) | |
| G16H 20/40 | (2018.01) | |
| G16H 40/63 | (2018.01) | |
| A61M 16/10 | (2006.01) | |
| A61B 5/087 | (2006.01) | |
| A61B 5/00 | (2006.01) | |

(52) U.S. Cl.
CPC ........ *A61M 16/024* (2017.08); *A61M 16/026* (2017.08); *G05B 17/02* (2013.01);
(Continued)

(58) Field of Classification Search
CPC .......... A61M 16/0057; A61M 16/0066; A61M 16/0069; A61M 16/024; A61M 16/026;
(Continued)

(56) References Cited

U.S. PATENT DOCUMENTS

| | | |
|---|---|---|
| 3,896,800 A | 7/1975 | Cibulka |
| 5,161,525 A | 11/1992 | Fennema et al. |

(Continued)

FOREIGN PATENT DOCUMENTS

| | | |
|---|---|---|
| EP | 2106819 A1 | 10/2009 |
| JP | 2008000436 A | 1/2008 |

OTHER PUBLICATIONS

International Search Report for PCT/EP2018/068872 dated Jul. 12, 2018.

*Primary Examiner* — Kendra D Carter
*Assistant Examiner* — Mautin I Ashimiu
(74) *Attorney, Agent, or Firm* — Daniel H. Brean

(57) ABSTRACT

A respiratory monitoring system includes (10) a mechanical ventilator (12) configurable to perform a ventilation mode in that includes an inhalation gas delivery phase and provides extrinsic positive end-expiratory pressure (PEEP) at a PEEP level during an exhalation phase. A breathing tubing circuit (26) includes: a patient port (28), a gas inlet line (16) connected to supply gas from the mechanical ventilator to the patient port, a gas flow meter (30) connected to measure gas flow into lungs of the patient, and a pressure sensor (32) connected to measure gas pressure at the patient port. At least one processor (38) is programmed to: compute a proxy pressure comprising an integral of gas flow into the lungs measured by the gas flow meter; and trigger the inhalation gas delivery phase of the ventilation mode when the proxy pressure decreases below a trigger pressure threshold.

15 Claims, 3 Drawing Sheets

(52) U.S. Cl.
CPC ............ *G16H 20/40* (2018.01); *G16H 40/63* (2018.01); *A61M 2016/003* (2013.01); *A61M 2016/0027* (2013.01); *A61M 2205/52* (2013.01); *A61M 2230/40* (2013.01)

(58) Field of Classification Search
CPC .... A61M 2016/0027; A61M 2016/003; A61M 2230/40
See application file for complete search history.

(56) References Cited

U.S. PATENT DOCUMENTS

| | | | |
|---|---|---|---|
| 5,390,666 A | 2/1995 | Fennema et al. | |
| 5,660,171 A | 8/1997 | Fennema et al. | |
| 6,240,920 B1 | 6/2001 | Stroem | |
| 6,390,091 B1 | 5/2002 | Banner et al. | |
| 6,837,241 B2 | 1/2005 | Samzelius | |
| 7,237,205 B2 | 6/2007 | Sarel | |
| 8,272,380 B2 | 9/2012 | Aviano et al. | |
| 8,434,480 B2 | 5/2013 | Aviano et al. | |
| 9,974,911 B2 | 5/2018 | Berthon-Jones | |
| 2007/0265427 A1 | 11/2007 | Hirakawa et al. | |
| 2009/0241951 A1 | 10/2009 | Aviano et al. | |
| 2012/0167884 A1 | 7/2012 | Cardelius | |
| 2012/0247471 A1* | 10/2012 | Masic | A61M 16/026 128/204.23 |
| 2014/0034054 A1 | 2/2014 | Angelico et al. | |
| 2014/0048072 A1 | 2/2014 | Angelico et al. | |
| 2014/0296730 A1 | 10/2014 | Stendqvist | |
| 2018/0353717 A1 | 12/2018 | Buschke et al. | |

* cited by examiner

VENTILATOR GAS DELIVERY INITIATION VIA A VIRTUAL PRESSURE TRIGGERING MECHANISM

CROSS-REFERENCE TO PRIOR APPLICATIONS

This application claims the priority benefit under 35 U.S.C. § 371 of International Patent Application No. PCT/EP2018/068872, filed on Jul. 12, 2018, which claims the priority benefit of U.S. Provisional Patent Application No. 62/533,691, filed on Jul. 18, 2017, the contents of which are herein incorporated by reference.

FIELD

The following relates to the medical therapy arts, respiratory therapy arts, medical ventilation arts, and related arts.

BACKGROUND

Detection of a patient's desire to initiate gas delivery during ventilation of the patient has been done in the industry using two primary methodologies. These are referred to as pressure triggering and flow triggering based on pressure and flow signals, respectively. When using the pressure triggering mechanism, initiation of the inhalation gas delivery phase occurs when the pressure at the patient port of the breathing tubing circuit, is reduced by the patient's effort below a pressure threshold previously set by the therapist.

During the use of the pressure triggering method, modern ventilators suspend gas delivery supply to the patient-tubing system throughout the duration of the exhalation phase of the breath cycle. Thus, when the patient initiates an effort to breathe, gas is made to flow between the tubing circuit and the patient lungs since the patient effort lowers the pressure in his/her lungs below the pressure level present in the tubing circuit. As gas migrates to the lung and the tubing circuit gets depleted, the pressure in the tubing circuit descends. When that pressure becomes less than a pre-determined threshold, selected by the care giver, the ventilator initiates the inhalation gas delivery phase in accordance with gas delivery targets appropriate for the ventilation modality (also pre-selected by the care giver).

Modern ventilators typically provide a pressure sensitivity setting (with a typical range: 0.5 to 20 cmH$_2$O with a resolution of 0.5 cmH$_2$O) which allows the practitioner to set the appropriate pressure threshold level for triggering the inhalation gas delivery phase.

A complication arises if the mechanical ventilation is configured to maintain a positive pressure at the end of expiration. In one approach for this instance, the ventilator's mechanism for triggering/initiation of the inhalation gas delivery phase of a breath uses the threshold selected and the Positive End Expiratory Pressure (PEEP) level setting (the reference point). If a difference between pre-set threshold and the PEEP level setting is less than or equal to the pressure measured at the tubing circuit's patient port, then gas delivery is initiated. Otherwise, the pressure at the patient port continues to be monitored.

The following provides new and improved apparatuses and methods which overcome the foregoing problems and others.

BRIEF SUMMARY

In accordance with one aspect, a respiratory monitoring system includes a mechanical ventilator configurable to perform a ventilation mode that includes an inhalation gas delivery phase and provides extrinsic positive end-expiratory pressure (PEEP) at a PEEP level during an exhalation phase. A breathing tubing circuit includes: a patient port, a gas inlet line connected to supply gas from the mechanical ventilator to the patient port, a gas flow meter connected to measure gas flow into lungs of the patient, and a pressure sensor connected to measure gas pressure at the patient port. At least one processor is programmed to: compute a proxy pressure comprising an integral of gas flow into the lungs measured by the gas flow meter; and trigger the inhalation gas delivery phase of the ventilation mode when the proxy pressure decreases below a trigger pressure threshold.

In accordance with another aspect, a non-transitory computer readable medium stores instructions executable by at least one electronic processor to perform a respiratory monitoring method. The method includes: computing a proxy pressure comprising an integral of gas flow into the lungs measured by an gas flow meter of a breathing tubing circuit operably connected to a mechanical ventilator configurable to perform a ventilation mode that includes an inhalation gas delivery phase and provides extrinsic positive end-expiratory pressure (PEEP) at a PEEP level; and triggering the inhalation gas delivery phase of the ventilation mode when the proxy pressure decreases below a trigger pressure threshold.

In accordance with another aspect, a respiratory monitoring system includes a mechanical ventilator configurable to perform a ventilation mode that includes an inhalation gas delivery phase and provides extrinsic positive end-expiratory pressure (PEEP) at a PEEP level. A breathing tubing circuit includes: a patient port, a gas inlet line connected to supply gas from the mechanical ventilator to the patient port, and a gas flow meter connected to measure gas flow into lungs of the patient, a pressure sensor connected to measure gas pressure at the patient port. At least one processor is programmed to: compute a proxy pressure comprising an integral of gas flow into the lungs or gas flow supplied by the mechanical ventilator, the proxy pressure computed by the equation:

$$P_{prox}(t) = PEEP - \int_{T_0}^{t_f} \frac{Q_{lung}(t)}{C_{tube}} dt$$

where $P_{prox}(t)$ is the proxy pressure; PEEP is the extrinsic PEEP level; $T_o$ is a time at which the pressure measured by the pressure sensor at the patient port reaches PEEP; $T_f$ is a time at which an inhalation phase starts, $Q_{lung}(t)$ is the measured gas flow into the lungs or an estimated gas flow supplied by the mechanical ventilator and $C_{tube}$ is a tubing circuit compliance of the breathing tubing circuit; and trigger the inhalation gas delivery phase of the ventilation mode when the proxy pressure decreases below a trigger pressure threshold.

One advantage resides in improved monitoring of a pressure level in a patient during ventilation.

Another advantage resides in facilitating the use of pressure triggering of the inhalation gas delivery phase in the case of ventilation employing an active controller for the Positive End Expiratory Pressure (PEEP) maintained, during exhalation, via flow delivered to the patient tubing system by the mechanical ventilator to avoid auto-triggering of the ventilator in the presence of leakages of the disclosed patient tubing system, since the triggering process of the disclosed patient tubing system is not as sensitive to leaks as other triggering methods.

Another advantage resides in providing such pressure triggering in the case of ventilation employing a PEEP setting maintained by delivered gas flow, in which the pressure threshold for triggering the inhalation gas delivery phase is sensibly related to (and in some embodiments equal to) the threshold that would be used if PEEP were maintained passively by modulating or closing off the exhalation valve.

Further advantages of the present disclosure will be appreciated to those of ordinary skill in the art upon reading and understand the following detailed description. It will be appreciated that any given embodiment may achieve none, one, more, or all of the foregoing advantages and/or may achieve other advantages.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
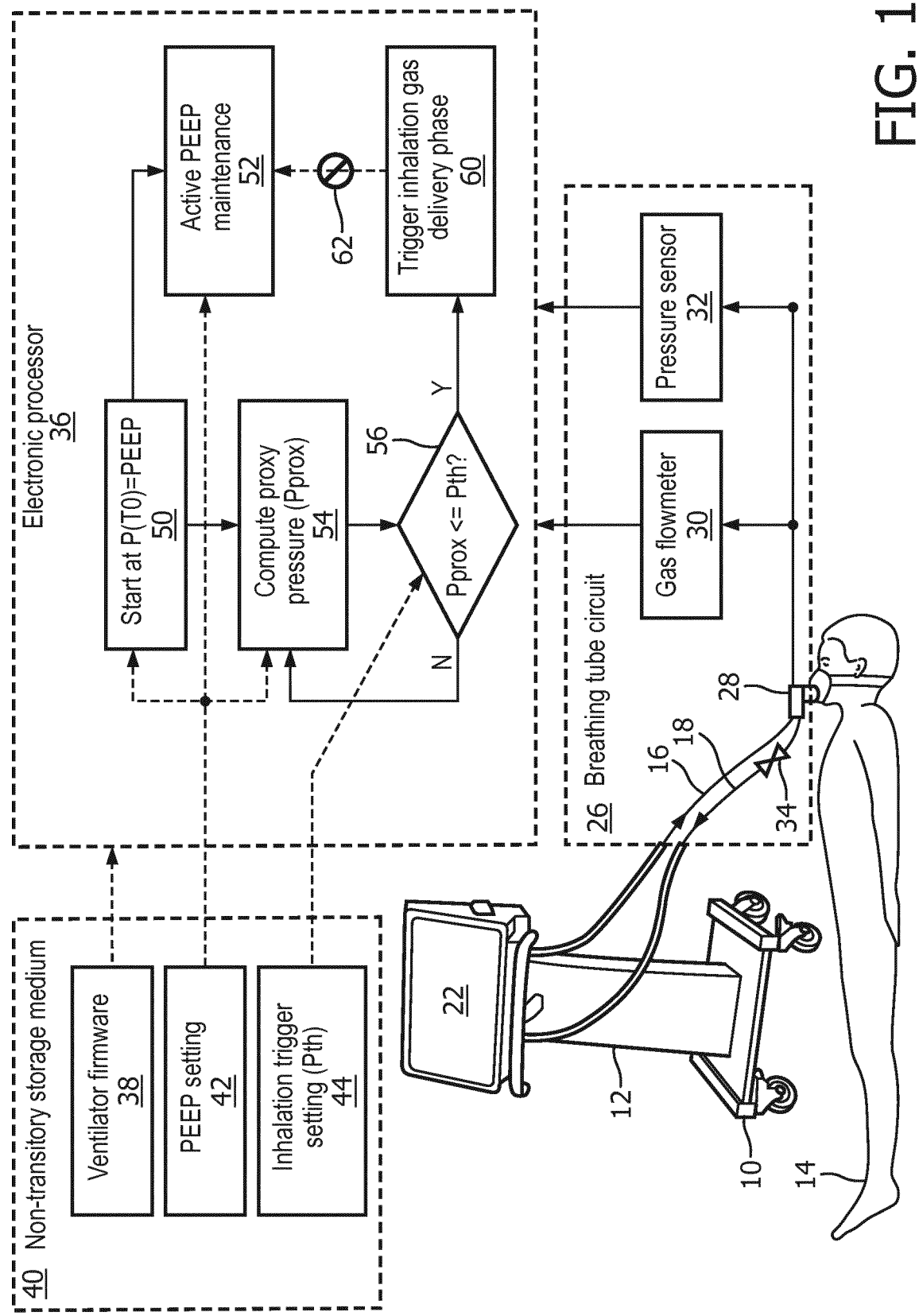
FIG. 1 shows a schematic of a proposed ventilator apparatus in accordance with one aspect of the present disclosure.

The following relates to an improvement in the triggering of the inhalation gas delivery phase in the context of mechanical ventilation. Traditionally, there are two approaches for this triggering. In pressure-based triggering, onset of spontaneous inspiration is detected as a decrease in pressure at the patient port of the breathing tubing circuit to a value below a triggering threshold. In flow-based triggering, onset of spontaneous inspiration is detected as an increase in positive gas flow into a disclosed patient-tubing system above a triggering threshold.

A difficulty arises if the ventilation system is designed to provide a controlled extrinsic positive end-expiratory pressure (PEEP). This is done for some patients in order to avoid alveolar collapse due to a low pressure level in the lungs. There are two approaches for this. In a valve-based approach, the exhalation valve is closed when PEEP is reached, so that the volume of gas in the breathing circuit is held constant. Here there is no particular difficulty in pressure-based triggering because the pressure will decrease as inhalation begins.

However, in some ventilation systems, such as blower based systems, the maintenance of PEEP can be done actively, by keeping the exhalation valve at least partially open and delivering gas flow via the blower to maintain the target PEEP value. Here, the pressure-based triggering is ineffective since the inhalation effort is simply offset by increased blower flow. Thus, in this operational mode the usual approach is to employ flow-based triggering.

While flow-based triggering is generally effective, it is recognized herein that one difficulty that can arise is flow noise induced triggering. With a blower based ventilator, noise in the breathing circuit generally manifests as flow fluctuations, and if these are too large they can induce spurious triggering of the inhalation gas delivery phase leading to loss of synchronicity with the patient's spontaneous inspiration effort.

A solution to the above-described problem is the triggering of inhalation flow based on a calculated "virtual" or "proxy" pressure decrease. In one embodiment, the virtual or proxy pressure calculation is given by $$P_{prox} = PEEP - \int_{t=T_o}^{t=T_1} Q\text{Lung } dt / C_{tube}$$

where PEEP is the extrinsic PEEP which is a ventilation parameter, $T_o$ is the time at which the pressure measured by the pressure sensor at the patient port reaches PEEP (so that $P_{prox}(t=T_o)=PEEP$), and $Q_{lung}(t)$ is the gas flow into the lungs measured by a flow sensor (Qlung (t) is positive when the gas flow is directed into the lungs). The term $C_{tube}$ is the tubing circuit compliance which may be provided by the ventilator circuit manufacturer or can be measured empirically using the relationship $C=\Delta V/\Delta P$ where $\Delta P$ is a pressure change measured for a volume of gas $\Delta V$ delivered to the tubing system.

The inhalation gas delivery phase is then triggered when the proxy pressure Pprox(t) decreases to below a threshold pressure, i.e. when Pprox(t=T1)=$P_{th}$ (where $P_{th}$ is some value below PEEP). Advantageously, the proxy pressure mimics the pressure that would actually be measured if the exhalation valve were to be completely closed in order to passively establish PEEP. That is, the proxy pressure is an estimation of the pressure drop that would have been caused by the patient's effort to breathe if PEEP control had operated by completely closing off the exhalation valve. Thus, for example, $P_{th}$ can be set to the "standard" value used for that type of triggering mechanism when active PEEP control methodology is used.

With reference to FIG. 1, an embodiment of a respiratory therapy apparatus 10 is shown, which includes a mechanical ventilator 12 configured to deliver mechanical ventilation to a patient 14. Thus, the respiratory monitoring system 10 may also be referred to as a mechanical ventilation system or apparatus.

The respiratory therapy apparatus 10 is used to provide mechanical ventilation to a patient via the mechanical ventilator 12 that delivers gas flow and/or pressure in accordance with ventilator settings to a ventilated patient 14 via a inlet gas line 16. Exhaled gas returns to the ventilator 12 via an exhalation gas hose 18. A patient port 28, which in the illustrative embodiment is a Y-piece or alternatively may be a tracheal tube, or in some cases a full-face mask) couples gas from the discharge end of the inlet gas line 16 to the ventilated patient 14 during inhalation and couples exhaled gas from the ventilated patient 14 into the exhalation gas line 18 during exhalation. Not shown in FIG. 1 are numerous other ancillary components that may be provided depending upon the ventilation mode and other therapy being received by the ventilated patient 14. Such ancillary components may include, by way of illustration: an oxygen bottle or other medical-grade oxygen source for delivering a controlled level of oxygen to the gas flow, usually controlled by a Fraction of Inspired Oxygen (FiO$_2$) ventilator setting; a humidifier plumbed into the inlet line 16; a nasogastric tube to provide the patient 14 with nourishment; and so forth. The mechanical ventilator 12 has a user interface including, in the illustrative example, a touch-sensitive display 22 via which the physician, respiratory specialist, or other medical personnel can visualize the ventilator settings and monitor measured variables (e.g., gas way pressure and gas flow) and operating parameters of the mechanical ventilator 12. Additionally or alternatively, the user interface may include physical user input controls (buttons, dials, switches, et cetera), a keyboard, a mouse, audible alarm device(s), indicator light(s), or so forth.

As shown in FIG. 1, the mechanical ventilation apparatus 10 includes a breathing tubing circuit 26 which includes the inlet line 16 and the outlet line 18, along with the patient port 28, a gas flow meter 30, a pressure sensor 32, and an exhalation valve 34. The gas flow meter 30 and the pressure sensor 32 can each be hardware sensors known in the art. The gas inlet line 16 is connected to supply gas from the mechanical ventilator 12 to the patient port 28. The patient port 28 can be secured or otherwise attached to the Y piece. The gas flow meter 30 is shown diagrammatically, and is connected to measure gas flow into lungs of the patient, e.g. by measuring gas or gas flow into the inlet of the patient port 28 or gas flow or gas flow in the inlet line 16. The pressure sensor 32 is likewise diagrammatically shown, and is connected to measure gas pressure at the patient port 28. The illustrative exhalation valve 34 is shown mounted on the outlet line 18, but may alternatively be integrated into the patient port 28 or internal to the ventilator 12. The exhalation valve is configured to regulate expiration of gas or gas from the lungs of the patient via the gas outlet line 18, e.g. if the exhalation valve 34 is completely closed then no exhalation gas can flow from the patient port 28 through the outlet line 18; while, a partially closed setting of the exhalation valve 34 can introduce a controlled resistance to the exhalation gas or gas flow.

The mechanical ventilator 12 also includes an electronic processor 36 for controlling the ventilation cycling by executing firmware 38 stored in a non-transitory storage medium 40 such as a read only memory (ROM), electronically programmable ROM (EPROM), flash memory, solid state drive (SSD), or other electronic storage medium; or a magnetic disk or other magnetic storage medium. The non-transitory storage medium 40 further stores ventilator parameters or settings, such as the ventilation mode (e.g. pressure support ventilation or PSV as one non-limiting illustrative example), parameters of that ventilation mode (e.g. the support pressure setting in the illustrative PSV mode), or so forth. The electronic processor 36 can be, for example, a microprocessor, an application-specific integrated circuit (ASIC), or a suitable hardware controller known in the art.

In illustrative FIG. 1, two salient settings are shown: an extrinsic positive end-expiratory pressure (PEEP) setting 42, and a trigger pressure threshold ($P_{th}$) 44, which controls (in conjunction with a proxy pressure as disclosed herein) the triggering of an inhalation gas delivery phase of a ventilation mode. The PEEP setting 42 and the trigger pressure threshold 44 may be input to the respiratory therapy system 10 via the user interface, or by additional automatic controls which determine appropriate values based on known patient characteristics. It should be noted that while FIG. 1 diagrammatically depicts a single non-transitory storage medium 40, more generally there may be more than one such medium. For example, in some embodiments the firmware 38 is stored on a different non-transitory storage medium than the ventilator settings 42, 44. Furthermore, the electronic processor 36 is operatively connected to receive measurements (e.g. samples) from the sensors 30, 32 as well as from other components of the mechanical ventilator 12 or that are operatively communicating with the ventilator 12, e.g. a supplementary oxygen supply, physiological sensors (e.g. heart rate monitor, pulse oximeter), and/or so forth. Typically, the electronic processor 36 and non-transitory storage medium 40 are on-board components of the mechanical ventilator 12 so as to facilitate hard-wired connections providing high reliability; however, more distributed arrangements in which components are operatively connected by external wiring (e.g. USB cables) or wireless connections (e.g. Bluetooth™) are alternatively contemplated.

With continuing reference to FIG. 1, in an illustrative ventilation process implemented by the ventilator 12, it is assumed that the ventilator 12 is performing mechanical ventilation which includes an inhalation gas delivery phase during which positive pressure is applied by the ventilator 12 to the patient port 28 via the inlet hose 16; an expiration phase during which the patient exhales; and during which the ventilator 12 actively maintains an extrinsic positive end-expiratory pressure (PEEP) at the patient port 28. Moreover, it is assumed, in the embodiments described herein, that the ventilator actively maintains the extrinsic PEEP by applying positive pressure to the patient port 28 to maintain the pressure at the programmed PEEP setting 42.

Furthermore, the illustrative ventilation process employs pressure triggering using the trigger pressure threshold 44. However, this process is complicated by the use of active extrinsic PEEP maintenance. To see why, the situation for passive PEEP maintenance is considered first.

If the ventilator maintained PEEP at the PEEP setting 42 passively, it would do so by modulating and eventually completely closing the exhalation valve 34 when the expiration phase caused the pressure to decrease to the PEEP setting 42. With the exhalation valve 34 closed, the gas volume is fixed and hence the pressure measured by the pressure sensor 32 will be approximately constant. In this case of passive PEEP maintenance, pressure triggering of the next inhalation gas delivery phase (that is, the inhalation gas delivery phase of the next breathing cycle starting after closure of end-expiration) would be a straightforward matter of monitoring the pressure via the pressure sensor 32 and triggering the inhalation gas delivery phase when the measured pressure decreased below the trigger pressure threshold 44. This pressure decrease will result naturally because as the patient engages in incipient inhalation, this expands the lungs thereby increasing the volume and consequently decreasing the pressure. The pressure threshold 44 is programmed by the respiratory clinician based on expert knowledge of the particular patient's spontaneous respiration capability together with the known PEEP setting 42, e.g. a lower $P_{th}$ setting is typically programmed for a patient with weaker respiratory capability, and $P_{th}$ is always lower than the PEEP setting 42. In general the $P_{th}$ setting may also be tuned by trial and error as the respiratory clinician reviews the patient's breathing as measured by the flow and pressure sensors 30, 32.

This approach is not applicable in the case of active extrinsic PEEP maintenance, because in this case as the patient begins to inhale to initiate the next spontaneous breath, the decrease in pressure that would be produced by the spontaneous inhalation is canceled by increased positive pressure applied by the mechanical ventilator 12 in order to control the pressure, using the reading of the pressure sensor 32, at the programmed PEEP setting 42. Conventionally, this has caused the respiratory clinician to elect to employ flow triggering, which will remain operative with active extrinsic PEEP maintenance since the gas flow will indeed increase due to both the patient's spontaneous inhalation and the extra pressure applied by the ventilator 12. However, if there is noise in the breathing circuit 26, for example, caused by condensate water slushing around in the tubing system, this noise generally manifests as flow fluctuations. If these flow fluctuations are too large they can induce spurious flow-based triggering of the inhalation gas delivery phase leading to loss of synchronicity with the patient's spontaneous inspiration effort. The potential for noise is enhanced in the instant case because there are two sources of gas flow: the patient's spontaneous inhalation effort and the positive pressure applied by the ventilator 12 to maintain extrinsic PEEP.

With continuing reference to FIG. 1, an improved approach for pressure triggering of the inhalation gas delivery phase is disclosed, which is operative in the case of active extrinsic PEEP regulation. The approach is suitably performed by the electronic processor 36 of the mechanical ventilator 12 executing instructions stored at the non-transitory/volatile storage medium 40 (e.g. the firmware 38) and read and executed by the electronic processor 36. In an operation 50, the pressure read by the pressure sensor 32 is monitored during the exhalation phase to detect when the decreasing pressure falls to the level of the programmed PEEP setting 42. This triggers the end of the exhalation phase. The time of the end of the exhalation phase, detected by the operation 50, is denoted herein as $T_0$. The exhalation phase includes executing an active PEEP maintenance process 52 that uses the pressure read by the pressure sensor 32, to control the pressure in the respiratory therapy system 10 to match the PEEP setting 42 by operations that include at least operating the blower or other gas flow generating device to apply positive pressure to the patient port 28 via the inlet hose 16. This PEEP maintenance process 52 is carried out throughout the exhalation phase. The pressure may cross the PEEP level and return to values above PEEP during the exhalation phase. The active PEEP maintenance process 52 may optionally include other control mechanisms, such as partially closing (or actively modulating) the exhalation valve 34 to increase (or modulate) flow resistance throughout the exhalation phase.

Concurrently with initiating the active PEEP maintenance 52, a proxy pressure ($P_{prox}$) monitoring process 54 is initiated. In some embodiments, the proxy pressure is intended to estimate the pressure that would have been observed in the case of a triggering effort by the patient during passive extrinsic PEEP regulation/control. The proxy pressure monitoring process 54 will be described in greater detail with reference to FIG. 2; however, the concept of the proxy pressure can be understood as follows. In the case of passive extrinsic PEEP maintenance, the PEEP control is carried out via control of the pressure measured by the pressure sensor 32 at the patient port 28 using modulation of the ventilator's exhalation valve 34. When in Pressure triggering mode, all gas supply to the patient tubing system is cut off during the exhalation phase and thus all the gas delivered to the patient's lungs, during a triggering effort, comes from the tubing system 26 itself. Therefore, for a system that uses active PEEP control to maintain the pressure level at the PEEP setting 42, via dynamic control of the gas supplied by the ventilator 12 to the patient port 28 via the inlet hose 16, it may be assumed that all the gas delivered to the patient lungs would have come from the tubing system (as in the case of the alternate passive PEEP control). Changes to the pressure in the tubing system 26 can be determined via the definition of the pneumatic compliance $C=\Delta V/\Delta P$ where $\Delta V$ is the volume change (integral of gas flow measured by the gas flow meter 30) and $\Delta P$ is the pressure change measured by the pressure sensor 32. Therefore, it is possible to estimate the "virtual" modification to the pressure level ($\Delta P$) in the tubing system as a function of the amount of gas delivered to the lung ($\Delta V$), in a ventilator that controls PEEP by dynamic supply of the gas delivered to the system, and effectively maintains the pressure in the Patient-tubing system at the pre-set PEEP level. To this end, the compliance definition can be rearranged as $\Delta P=\Delta V/C$. The volume change can be computed as $\Delta V(t)=\int_{T_o}^{t_f} Q_{lung}(\tau)d\tau$ where $Q_{lung}$ is the gas flow delivered to the lungs by the ventilator 12 and $\tau$ represents time in the integral (to distinguish from time $t_f$ which is the current time at which a new breath occurs and hence the end time of the integral). $T_o$ refers to a time at which the pressure at the patient port 28 crosses the PEEP level in a downward direction for the first time since the start of the exhalation phase. The compliance $C=C_{tube}$, that is, the compliance of the tubing circuit 26. This yields $$P_{prox}(t) = PEEP - \int_{T_0}^{t_f} \frac{Q_{lung}(\tau)}{C_{tube}} dt.$$

With continuing reference to FIG. 1, in a decision operation 56 it is determined whether the proxy pressure has decreased to the programmed threshold pressure setting 44. If it has not yet decreased to this threshold, flow returns to block 54 to continue monitoring the proxy pressure. When the decision operation 56 detects that the pressure threshold 44 has been reached, this triggers the next inhalation gas delivery phase (operation 60) for the next breath. This also entails triggering termination of the active PEEP regulation/control 52, as indicated by the automatic termination denoted in FIG. 1 by symbol 62.

Figure 2:
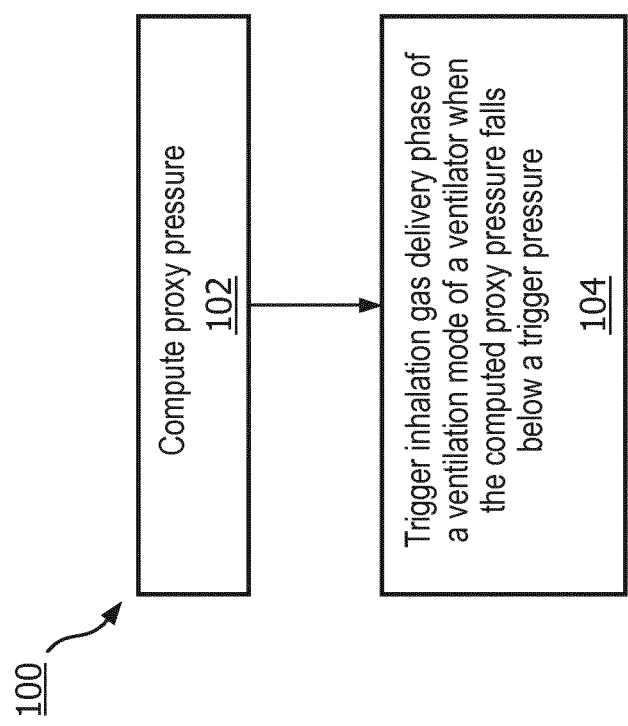
FIG. 2 shows a flow chart of an exemplary method of use for the ventilator apparatus of FIG. 1.

With reference to FIG. 2, the respiratory monitoring method 100 is diagrammatically shown as a flowchart. At 102, the electronic processor 38 is programmed to compute a proxy pressure comprising an integral of gas flow into the lungs measured by the gas flow meter 30. In some embodiments, the proxy pressure comprises the integral computed starting at a time when the gas pressure at the patient port 28 measured by the pressure sensor 32 decreases below a threshold. For example, this threshold is the PEEP level.

In other embodiments, the proxy pressure comprises the integral of gas flow into the lungs measured by the gas flow meter 30 scaled by a tubing circuit compliance value of the breathing tubing circuit. For example, the proxy pressure is calculated according to the equation:

$$P_{prox}(t) = PEEP - \int_{T_0}^{t} \frac{Q_{lung}(\tau)}{C_{tube}} d\tau \qquad \text{Equation 1}$$

where $P_{prox}(t)$ is the proxy pressure; PEEP is the extrinsic PEEP level; $T_o$ is a time at which the pressure measured by the pressure sensor 32 at the patient port reaches PEEP; $Q_{lung}(t)$ is the gas flow into the lungs measured by the gas flow meter 30; and $C_{tube}$ is a tubing circuit compliance of the breathing tubing circuit 26. In other examples, the processor 38 is programmed to compute the integral of flow into the lungs measured by the gas flow meter using a rectangular or trapezoidal numerical integration.

Figure 3:
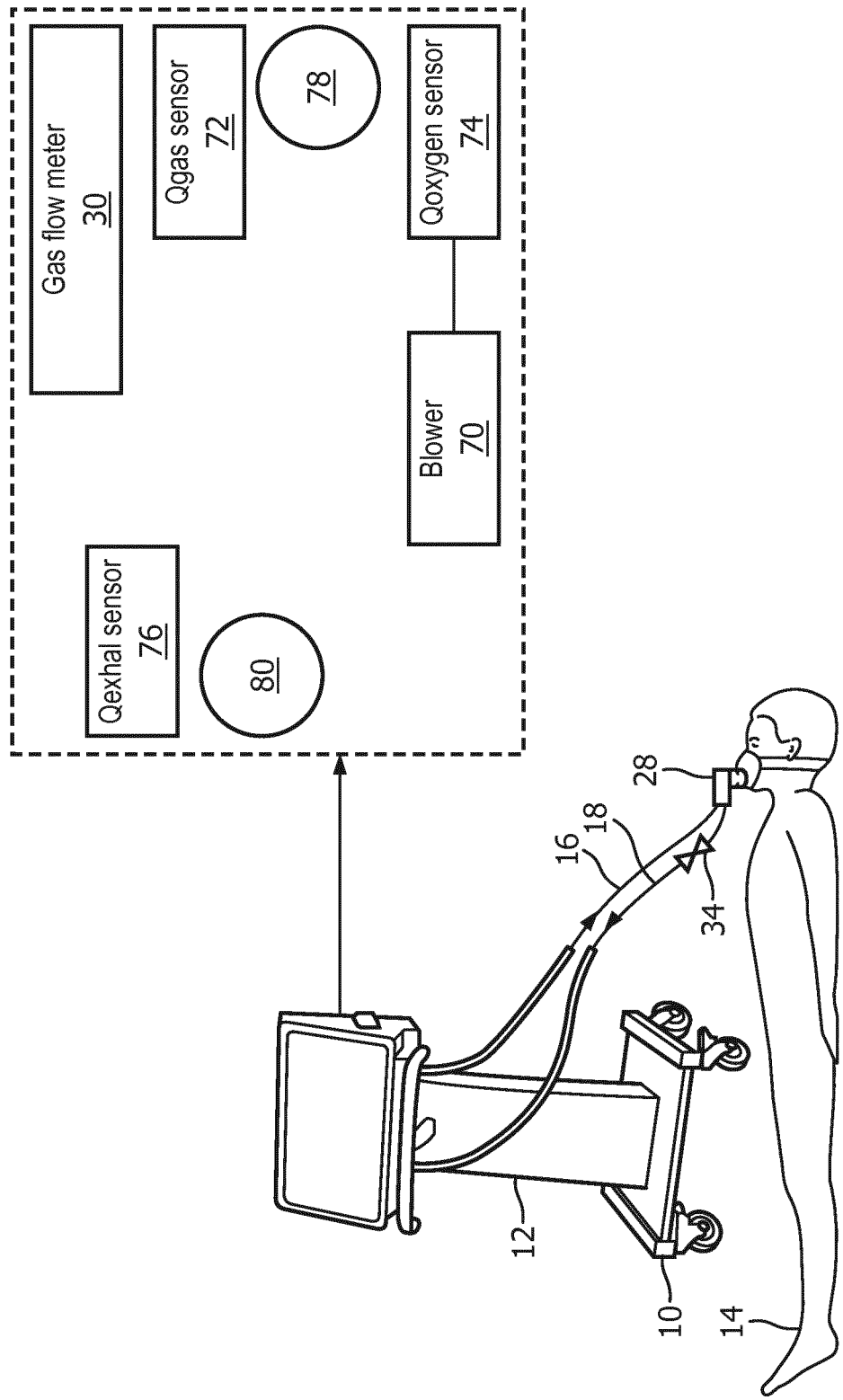
FIG. 3 shows a schematic of a proposed ventilator apparatus in accordance with another aspect of the present disclosure.

In a further embodiment, as shown in FIG. 3, the proxy pressure comprises the integral of flow supplied by the mechanical ventilator 12 to the inlet line 16 such that gas flow leakages are taken into account. In this embodiment, since the gas flow supplied by the mechanical ventilator 12 includes the leakage flow and the lung flow, the system 10 does not need the gas flow meter 30 to be positioned at the patient port 28, but rather gas and oxygen flow sensors can be located in the proximity of the gas and oxygen (if available) sources 70 (i.e., a blower and an oxygen source) of the respiratory therapy system 10. In this example, $Q_{lung}(t)$ is equal to the sum of the leakage gas flow and the lung gas flow.

In this embodiment, the gas flow meter 30 can comprise three different sensors: a gas flow sensor 72 configured to measure air gas flow (e.g., $FiO_2=21\%$); an $O_2$ flow sensor 74 configured to measure oxygen gas flow; and an exhalation gas flow sensor 76 configured to measure flow of gas exhaled by the patient (air mixed with the oxygen supplied by the ventilator 12). The lung flow can be estimated using Equation 2:

$$Q_{Lung}=Q_{air}+Q_{O2}-Q_{exhalation}-Q_{leak}-Q_{tube} \qquad \text{Equation 2}$$

where: $Q_{air}$ and $Q_{O2}$ are flows measured by the sensors 72 and 74, which are located a gas outlet port 78 internal to the ventilator 12. $Q_{exhalation}$ is a flow measured from the sensor 76 located on the inlet port, 80 internal to the ventilator 12 adjacent the exhalation valve 34. $Q_{leak}$ is a value estimated from Equation 3:

$$Q_{leak}=G_{Leak}*(P_p)^{0.5} \qquad \text{Equation 3}$$

in which is $Q_{Leak}$ estimate of the gas exiting a leak orifice (i.e., at the patient port 28); $G_{Leak}$ is a conductance coefficient for the leak orifice; and $P_p$ is a pressure measured by the pressure sensor 32. $Q_{tube}$ is a value estimated using Equation 4:

$$Q_{tube}=C_{tube}*d(P_p)/dt \qquad \text{Equation 4}$$

in which $Q_{tube}$ is estimate of the gas used in pressurizing or depressurizing the system 10; $d(P_p)/dt$ is a measure of an expansion or contraction of a tube (e.g., the inlet or outlet line 16 or 18).

At 104, once the proxy pressure is computed, the processor 38 is programmed to trigger an inhalation gas delivery phase of a ventilation mode when the proxy pressure decreases below a trigger pressure. For example, the mechanical ventilator 12 is configured to perform a ventilation mode that includes an inhalation gas delivery phase and provides extrinsic positive end-expiratory pressure (PEEP) at a PEEP level. To do so, the mechanical ventilator 12 is configured to set the exhalation valve 34 to at least partially open setting. Simultaneously, the mechanical ventilator 12 is configured to supply gas to the patient port 28 at a gas flow controlled to maintain the pressure at the patient port measured by the pressure sensor 32 at the PEEP level. A trigger pressure at which the ventilation mode occurs is lower than the PEEP level.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A respiratory monitoring system, comprising:
  a mechanical ventilator configurable to perform a ventilation mode that includes an inhalation gas delivery phase and provides extrinsic positive end-expiratory pressure (PEEP) at a PEEP level during an exhalation phase;
  a breathing tubing circuit including:
    a patient port,
    a gas inlet line connected to supply gas from the mechanical ventilator to the patient port,
    a gas flow meter connected to measure gas flow into lungs of the patient,
    a pressure sensor connected to measure gas pressure at the patient port, and
  at least one processor programmed to:
    compute a proxy pressure comprising an integral of gas flow into the lungs measured by the gas flow meter; and
    trigger the inhalation gas delivery phase of the ventilation mode when the proxy pressure decreases below a trigger pressure threshold.

2. The system of claim 1, wherein the proxy pressure comprises the integral computed starting at a time when the gas pressure at the patient port measured by the pressure sensor decreases below a start threshold.

3. The system of claim 2, wherein the start threshold is the PEEP level.

4. The system of claim 1, further including:
  an exhalation valve configured to regulate expiration of gas from the lungs of the patient;
  wherein the mechanical ventilator is configurable to perform the ventilation mode including providing the extrinsic PEEP at the PEEP level by setting or controlling the exhalation valve to an at least partially open setting while simultaneously supplying gas to the patient port at an gas flow controlled to maintain the gas pressure at the patient port measured by the pressure sensor at the PEEP level.

5. The system of claim 4, wherein the trigger pressure is lower than the PEEP level.

6. The system of claim 1, wherein the proxy pressure comprises the integral of gas flow into the lungs measured by the gas flow meter scaled by a tubing circuit compliance value of the breathing tubing circuit.

7. The system of claim 1, when the proxy pressure comprises:

$$P_{prox}(t) = PEEP - \int_{T_0}^{tf} \frac{Q_{lung}(t)}{C_{tube}} dt$$

where $P_{prox}(t)$ is the proxy pressure; PEEP is the extrinsic PEEP level; $T_o$ is a time at which the pressure measured by the pressure sensor at the patient port reaches PEEP; $T_f$ is a time at which an inhalation phase starts, $Q_{lung}(t)$ is the gas flow into the lungs measured by the gas flow meter; and $C_{tube}$ is a tubing circuit compliance of the breathing tubing circuit.

8. The system of claim 1, wherein the at least one processor is programmed to:
  compute the integral of gas flow into the lungs measured by the gas flow meter using a rectangular or trapezoidal numerical integration.

9. A non-transitory computer readable medium storing instructions executable by at least one electronic processor to perform a respiratory monitoring method, the method comprising:
  computing a proxy pressure comprising an integral of gas flow into the lungs measured by a gas flow meter of a breathing tubing circuit operably connected to a mechanical ventilator configurable to perform a ventilation mode that includes an inhalation gas delivery phase and provides extrinsic positive end-expiratory pressure (PEEP) at a PEEP level; and triggering the inhalation gas delivery phase of the ventilation mode when the proxy pressure decreases below a trigger pressure threshold.

10. The non-transitory computer readable medium of claim 9, wherein the respiratory monitoring method further includes:

with the at least one electronic processor, computing the proxy pressure comprising the integral starting at a time when the gas pressure at the patient port measured by a pressure sensor of the breathing tubing circuit decreases below a threshold.

11. The non-transitory computer readable medium of claim 10, wherein the threshold is the PEEP level.

12. The non-transitory computer readable medium of claim 9, wherein the respiratory monitoring method further includes:

controlling the mechanical ventilator to perform the ventilation mode including providing the extrinsic PEEP at the PEEP level by setting or controlling an exhalation valve of the breathing tubing circuit to an at least partially open setting while simultaneously supplying gas to the patient port at a gas flow controlled to maintain the gas pressure at the patient port measured by the pressure sensor at the PEEP level.

13. The non-transitory computer readable medium of claim 12, wherein the trigger pressure is lower than the PEEP level.

14. The non-transitory computer readable medium of claim 9, wherein the respiratory monitoring method further includes:

with the at least one electronic processor, computing the proxy pressure as the integral of gas flow into the lungs measured by the gas flow meter scaled by a tubing circuit compliance value of the breathing tubing circuit.

15. The non-transitory computer readable medium claim 9, wherein the respiratory monitoring method further includes:

with the at least one electronic processor, computing the proxy pressure with an equation:

$$P_{prox}(t) = PEEP - \int_{T_0}^{t_f} \frac{Q_{lung}(t)}{C_{tube}} dt$$

where $R_{prox}(t)$ is the proxy pressure; PEEP is the extrinsic PEEP level; $T_o$ is a time at which the pressure measured by the pressure sensor at the patient port reaches PEEP; $T_f$ is a time at which an inhalation phase starts, $Q_{lung}(t)$ is the gas flow into the lungs measured by the gas flow meter; and $C_{tube}$ is a tubing circuit compliance of the breathing tubing circuit.

* * * * *